(12) United States Patent
Moon

(10) Patent No.: US 8,921,107 B2
(45) Date of Patent: Dec. 30, 2014

(54) METHOD FOR DIFFERENTIATING HUMAN NEURAL PROGENITOR CELLS INTO DOPAMINERGIC NEURONS, AND MEDIUM FOR DIFFERENTIATION THEREOF

(75) Inventor: Ji-Sook Moon, Seoul (KR)

(73) Assignee: College of Medicine Pochon Cha University Industry-Academic Corportaion Foundation, Gyeonggi-do (KR)

( * ) Notice: Subject to any disclaimer, the term of this patent is extended or adjusted under 35 U.S.C. 154(b) by 120 days.

(21) Appl. No.: 13/704,030

(22) PCT Filed: Jun. 7, 2011

(86) PCT No.: PCT/KR2011/004118
§ 371 (c)(1), (2), (4) Date: Dec. 13, 2012

(87) PCT Pub. No.: WO2011/159050
PCT Pub. Date: Dec. 22, 2011

(65) Prior Publication Data
US 2013/0089926 A1    Apr. 11, 2013

(30) Foreign Application Priority Data

Jun. 14, 2010  (KR) .................. 10-2010-0055832

(51) Int. Cl.
*C12N 5/08*   (2006.01)
(52) U.S. Cl.
USPC ........................................................ 435/368
(58) Field of Classification Search
USPC ............................... 435/368, 377, 404
See application file for complete search history.

(56) References Cited

U.S. PATENT DOCUMENTS 7,604,992 B2 *  10/2009  Reubinoff .................. 435/377
2009/0076019 A1 *  3/2009  Tyers et al. ............. 514/252.13

OTHER PUBLICATIONS

Lindner G. et al. Effect of Fusaric Acid on Nerve Tissue in Culture. Zeitschrift fuer Microskopisch Anatomische Forschung 100(2)262-272, 1986.*

Krabbe, et al., "Enhanced dopaminergic differentiation of human neural stem cells by synergistic effect of Bcl-XL and reduced oxygen tension", Journal of Neurochemistry, vol. 110, pp. 1908-1920, (2009).

Hidaka, et al., "Fusaric (5-Butylpicolinic) Acid, an Inhibitor of Dopamine β-Hydroxylase, affects Serotonin and Noradrenaline", Nature, vol. 231, pp. 54-55, (1971).

Sánchez-Pernaute, et al., "In Vitro Generation and Transplantation of Precursor-Derived Human Dopamine Neurons", Journal of Neuroscience Research, vol. 65, p. 284-288, (2001).

Perrier, et al., "Derivation of midbrain dopamine neurons from human embryonic stem cells", PNAS, vol. 101, No. 34, pp. 12543-12548, (2004).

Robertson, et al., "Neural stem cell engineering: directed differentiation of adult and embryonic stem cells into neurons", Front. Biosci., vol. 13, pp. 21-50, (2008).

Björklund, et al., "Reconstruction of the nigrostriatal dopamine pathway by intracerebral nigral transplants", Brain Research, vol. 177, pp. 555-560, (1979).

Perlow, et al., "Brain Grafts Reduce Motor Abnormalities Produced by Destruction of Nigrostriatal Dopamine System", Science, vol. 204, pp. 643-647, (1979).

Snyder, et al., "Stem cell treatment for Parkinson's disease: an update for 2005", Curr Opin Neurol, vol. 18, pp. 376-385, (2005).

Storch, et al., "Midbrain-derived neural stem cells: from basic science to therapeutic approaches", Cell Tissue Res, vol. 318, pp. 15-22, (2004).

Yang, et al., "Neural Stem Cells Spontaneously Express Dopaminergic Traits after Transplantation into the Intact or 6-Hydroxydopamine-Lesioned Rat", Experimental Neurology, vol. 177, pp. 50-60, (2002).

Riaz, et al., "The differentiation potential of human foetal neuronal progenitor cells in vitro", Developmental Brain Research, vol. 153, pp. 39-51, (2004).

Maciaczyk, et al., "Combined use of BDNF, ascorbic acid, low oxygen, and prolonged differentiation time generates tyrosine hydroxylase-expressing neurons after long-term in vitro expansion of human fetal midbrain precursor cells", Experimental Neurology, vol. 213, pp. 354-362, (2008).

\* cited by examiner

*Primary Examiner* — Ralph Gitomer
(74) *Attorney, Agent, or Firm* — Vorys, Sater, Seymour and Pease LLP; Mihsun Koh

(57) ABSTRACT

The present invention provides a method for differentiating human neural progenitor cells into dopaminergic neurons, comprising the step of culturing human neural progenitor cells in a medium containing fusaric acid. In addition, the present invention provides a medium for differentiation of human neural progenitor cells into dopaminergic neurons.

9 Claims, 9 Drawing Sheets

TH + cells

SEQUENCE LISTING

```
<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Sense primer

<400> SEQUENCE: 1
agccctacca agaccagacg                                           20

<210> SEQ ID NO 2
<211> LENGTH: 19
<212> TYPE: DNA
<213> ORGANISM: Artificial Sequence
<220> FEATURE:
<223> OTHER INFORMATION: Antisense primer

<400> SEQUENCE: 2
gcgtgtacgg gtcgaactt                                            19

<210> SEQ ID NO 3
<211> LENGTH: 20
<212> TYPE: DNA
<213> ORGANISM: Artificial Sequence
<220> FEATURE:
<223> OTHER INFORMATION: Sense primer

<400> SEQUENCE: 3
```

```
gggcctttgg acatctcttc                                              20

<210> SEQ ID NO 4
<211> LENGTH: 20
<212> TYPE: DNA
<213> ORGANISM: Artificial Sequence
<220> FEATURE:
<223> OTHER INFORMATION: Antisense primer

<400> SEQUENCE: 4
cctccgtgta gtgacccttg                                              20

<210> SEQ ID NO 5
<211> LENGTH: 21
<212> TYPE: DNA
<213> ORGANISM: Artificial Sequence
<220> FEATURE:
<223> OTHER INFORMATION: Sense primer

<400> SEQUENCE: 5
cagctggcgc acctcaagat g                                            21

<210> SEQ ID NO 6
<211> LENGTH: 23
<212> TYPE: DNA
<213> ORGANISM: Artificial Sequence
<220> FEATURE:
<223> OTHER INFORMATION: Antisense primer

<400> SEQUENCE: 6
agggaagttg ggctcaggac tgg                                          23

<210> SEQ ID NO 7
<211> LENGTH: 20
<212> TYPE: DNA
<213> ORGANISM: Artificial Sequence
<220> FEATURE:
<223> OTHER INFORMATION: Sense primer

<400> SEQUENCE: 7
gccgagtgga aactttgtc                                               20

<210> SEQ ID NO 8
<211> LENGTH: 20
<212> TYPE: DNA
<213> ORGANISM: Artificial Sequence
<220> FEATURE:
<223> OTHER INFORMATION: Antisense primer

<400> SEQUENCE: 8
gttcatgtgc gcgtaactgt                                              20

<210> SEQ ID NO 9
<211> LENGTH: 20
<212> TYPE: DNA
<213> ORGANISM: Artificial Sequence
<220> FEATURE:
<223> OTHER INFORMATION: Sense primer

<400> SEQUENCE: 9
acagcccaag atggtgactc                                              20

<210> SEQ ID NO 10
<211> LENGTH: 20
<212> TYPE: DNA
<213> ORGANISM: Artificial Sequence
```

```
<220> FEATURE:
<223> OTHER INFORMATION: Antisense primer

<400> SEQUENCE: 10
ccacgatgtc ctcactctca                                               20

<210> SEQ ID NO 11
<211> LENGTH: 20
<212> TYPE: DNA
<213> ORGANISM: Artificial Sequence
<220> FEATURE:
<223> OTHER INFORMATION: Sense primer

<400> SEQUENCE: 11
tgcttagccc aggactttca                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense primer

<400> SEQUENCE: 12
tgaagatgga gggagagctg                                               20

<210> SEQ ID NO 13
<211> LENGTH: 23
<212> TYPE: DNA
<213> ORGANISM: Artificial Sequence
<220> FEATURE:
<223> OTHER INFORMATION: Sense primer

<400> SEQUENCE: 13
ccaaagtggt ggacaagatt gcc                                           23

<210> SEQ ID NO 14
<211> LENGTH: 22
<212> TYPE: DNA
<213> ORGANISM: Artificial Sequence
<220> FEATURE:
<223> OTHER INFORMATION: Antisense primer

<400> SEQUENCE: 14
taactccgcc cattcactga cg                                            22

<210> SEQ ID NO 15
<211> LENGTH: 21
<212> TYPE: DNA
<213> ORGANISM: Artificial Sequence
<220> FEATURE:
<223> OTHER INFORMATION: Sense primer

<400> SEQUENCE: 15
atccagacca ccagaccaga g                                             21

<210> SEQ ID NO 16
<211> LENGTH: 21
<212> TYPE: DNA
<213> ORGANISM: Artificial Sequence
<220> FEATURE:
<223> OTHER INFORMATION: Antisense primer

<400> SEQUENCE: 16
ccccatccaa gagcaccaag g                                             21
```

```
<210> SEQ ID NO 17
<211> LENGTH: 22
<212> TYPE: DNA
<213> ORGANISM: Artificial Sequence
<220> FEATURE:
<223> OTHER INFORMATION: Sense primer

<400> SEQUENCE: 17
tgtcattctc agatgcaggc ac                                              22

<210> SEQ ID NO 18
<211> LENGTH: 19
<212> TYPE: DNA
<213> ORGANISM: Artificial Sequence
<220> FEATURE:
<223> OTHER INFORMATION: Antisense primer

<400> SEQUENCE: 18
tgaccgagtt aaggcgaac                                                  19

<210> SEQ ID NO 19
<211> LENGTH: 20
<212> TYPE: DNA
<213> ORGANISM: Artificial Sequence
<220> FEATURE:
<223> OTHER INFORMATION: Sense primer

<400> SEQUENCE: 19
tgcgtgccac atcaataaca                                                 20

<210> SEQ ID NO 20
<211> LENGTH: 25
<212> TYPE: DNA
<213> ORGANISM: Artificial Sequence
<220> FEATURE:
<223> OTHER INFORMATION: Antisense primer

<400> SEQUENCE: 20
aacatccttc actcagtatt gctaa                                           25

<210> SEQ ID NO 21
<211> LENGTH: 20
<212> TYPE: DNA
<213> ORGANISM: Artificial Sequence
<220> FEATURE:
<223> OTHER INFORMATION: Sense primer

<400> SEQUENCE: 21
cgaccaagac ctgcttttg                                                  20

<210> SEQ ID NO 22
<211> LENGTH: 20
<212> TYPE: DNA
<213> ORGANISM: Artificial Sequence
<220> FEATURE:
<223> OTHER INFORMATION: Antisense primer

<400> SEQUENCE: 22
attgcaacct gtgcaagacc                                                 20

<210> SEQ ID NO 23
<211> LENGTH: 20
<212> TYPE: DNA
<213> ORGANISM: Artificial Sequence
<220> FEATURE:
<223> OTHER INFORMATION: Sense primer
```

-continued

<400> SEQUENCE: 23
gggcaaaccc ttctcttctc                                               20

<210> SEQ ID NO 24
<211> LENGTH: 20
<212> TYPE: DNA
<213> ORGANISM: Artificial Sequence
<220> FEATURE:
<223> OTHER INFORMATION: Antisene primer

<400> SEQUENCE: 24
ggcactttgc actttcatca                                               20

<210> SEQ ID NO 25
<211> LENGTH: 20
<212> TYPE: DNA
<213> ORGANISM: Artificial Sequence
<220> FEATURE:
<223> OTHER INFORMATION: Sense primer

<400> SEQUENCE: 25
tgcttagccc aggactttca                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense primer

<400> SEQUENCE: 26
tgaagatgga gggagagctg                                               20

<210> SEQ ID NO 27
<211> LENGTH: 20
<212> TYPE: DNA
<213> ORGANISM: Artificial Sequence
<220> FEATURE:
<223> OTHER INFORMATION: Sense primer

<400> SEQUENCE: 27
cacgaaggag gagtgactgg                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense primer

<400> SEQUENCE: 28
tgtggcacac cactgacatt                                               20

METHOD FOR DIFFERENTIATING HUMAN NEURAL PROGENITOR CELLS INTO DOPAMINERGIC NEURONS, AND MEDIUM FOR DIFFERENTIATION THEREOF

This application is a National Stage application filed under Rule 371 based upon PCT/KR2011/004118 filed Jun. 7, 2011, which claims priority to Korean application 10-2010-0055832 filed Jun. 14, 2010.

The Sequence Listing submitted in text format (.txt) filed on Dec. 12, 2012, named "3_PX0081PCT_Sequence.txt", created on Dec. 3, 2012, 5.87 KB), is incorporated herein by reference.

TECHNICAL FIELD

The present invention relates to a method for differentiating human neural progenitor cells into dopaminergic neurons. More specifically, the present invention relates to a method for differentiating human neural progenitor cells into dopaminergic neurons, which comprises culturing human neural progenitor cells in a medium comprising fusaric acid. In addition, the present invention relates to a medium for differentiating human neural progenitor cells into dopaminergic neurons.

BACKGROUND ART

Parkinson's disease is characterized by the selective degeneration of dopaminergic neurons in the substantia nigra of the midbrain. Therapies using replacement of dopaminergic neurons in patients with Parkinson's disease through transplantation of fetal midbrain tissue are being variously studied (see Reference 1). Grafts of fetal midbrain tissue can survive for a long period in the human brain, restore dopaminergic innervation to the striatum in patients and reduce motor symptoms with Parkinson's disease (see Reference 2).

Although transplantation is a promising treatment for Parkinson's disease, its clinical application has been limited to a few cases, because it is very difficult to obtain large numbers of human abortion fetal tissues. To overcome this problem, various candidate cells have been investigated as possible donor cells for transplantation therapy for Parkinson's disease (see Reference 3).

Meanwhile, human neural progenitor cells (hNPCs) derived from fetal midbrain tissue appear to be a good candidate cell source for transplantation because of their capacity to self-renew for long-term proliferation activity and to differentiate into dopaminergic neurons (see References 4 and 5). Therefore, for treating Parkinson's disease through dopaminergic neuron replacement (i.e., transplantation), it is very important to establish an efficient method for the proliferation or expansion of hNPCs and an effective method for the differentiation of hNPCs into dopaminergic neurons.

Methods for the differentiation of hNPCs into dopaminergic neurons known in the prior arts include a differentiation method in a medium containing ascorbic acid and dibutyryl cyclic adenosine monophosphate (db-cAMP) for 3 days (see Reference 6); a differentiation method in a medium containing BDNF (brain-derived neurotrophic factor), dopamine, and forskolin for 3 weeks (see Reference 7); and a differentiation method in a medium containing SHH (sonic hedgehog), FGF-8 (fibroblast growth facter-8), BDNF (brain-derived neurotrophic factor), and ascorbic acid for 3 weeks (see Reference 8).

However, the differentiation methods according to the prior arts do not exhibit satisfactory differentiation potential; and require long duration for differentiation. And also, economic problems are incurred from the use of a medium containing expensive excipients, such as SHH, FGF-8, etc. The technology for the proliferation of a large number of cells required for treating the patients suffering from Parkinson's disease is still insufficient. Therefore, there are still a lot of limitations in the clinical applications thereof.

DISCLOSURE

Technical Problem

The present invention provides a method for differentiating human neural progenitor cells (hNPCs) into dopaminergic neurons, in high differentiation potential; and a medium useful for the differentiation. Especially, the present invention provides a method for differentiating hNPCs into dopaminergic neurons using fusaric acid as a differentiation inducing agent; and a medium useful for the differentiation.

Therefore, it is an object of the present invention to provide a method for differentiating human neural progenitor cells into dopaminergic neurons in a medium comprising a novel differentiation-inducing agent.

It is another object of the present invention to provide a differentiating medium useful for differentiating human neural progenitor cells into dopaminergic neurons.

Technical Solution

In accordance with an aspect of the present invention, there is provided a method for differentiating human neural progenitor cells into dopaminergic neurons, which comprises culturing human neural progenitor cells in a medium comprising fusaric acid.

In the method of the present invention, the medium may be prepared by adding fusaric acid to a medium for dopaminergic differentiation comprising dibutyryl cyclic adenosine monophosphate (db-cAMP), forskolin, B27, sonic hedgehog (SHH), and fibroblast growth factor 8 (FGF8).

Alternatively, in the method of the present invention, the medium may be a NB medium comprising fusaric acid, db-cAMP, forskolin, and B27, preferably a NB medium comprising 50 μM to 4 mM of fusaric acid, 50 μM to 4 mM of db-cAMP, 5 μM to 20 μM of forskolin, and 0.5% w/w to 5% w/w of B27. More preferably, the medium may be a NB medium comprising 100 μM of fusaric acid, 100 μM of db-cAMP, 10 μM of forskolin, and 2% w/w of B27.

In the method of the present invention, the culturing may be performed under a hypoxia condition having 2% to 10% of oxygen partial pressure.

In accordance with another aspect of the present invention, there is provided a medium for differentiating human neural progenitor cells into dopaminergic neurons, the medium of which is a NB media comprising fusaric acid, db-cAMP, forskolin, and B27.

The medium may be a NB medium comprising 50 μM to 4 mM of fusaric acid, 50 μM to 4 mM of db-cAMP, 5 μM to 20 μM of forskolin, and 0.5% w/w to 5% w/w of B27, preferably a NB medium comprising 100 μM of fusaric acid, 100 μM of db-cAMP, 10 μM of forskolin, and 2% w/w of B27.

Advantageous Effects

It is found by the present invention that, when human neural progenitor cells are cultured in the presence of fusaric acid, the differentiation into dopaminergic neurons is remarkably increased. Especially, the differentiation method of the present invention is cost effective, because human neural progenitor cells can be differentiated into dopaminergic neurons using inexpensive fusaric acid, instead of expensive differentiation-inducing agents, SHH and FGF8, that are of limited use. And also, the differentiation method of the present invention can remarkably improve the unsatisfactory differentiation potential according to the prior art methods. Therefore, the differentiation method of the present invention can be applied to the manufacture of dopaminergic neurons for treating neuronal damages including Parkinson's disease.

BEST MODE

Figure 1:
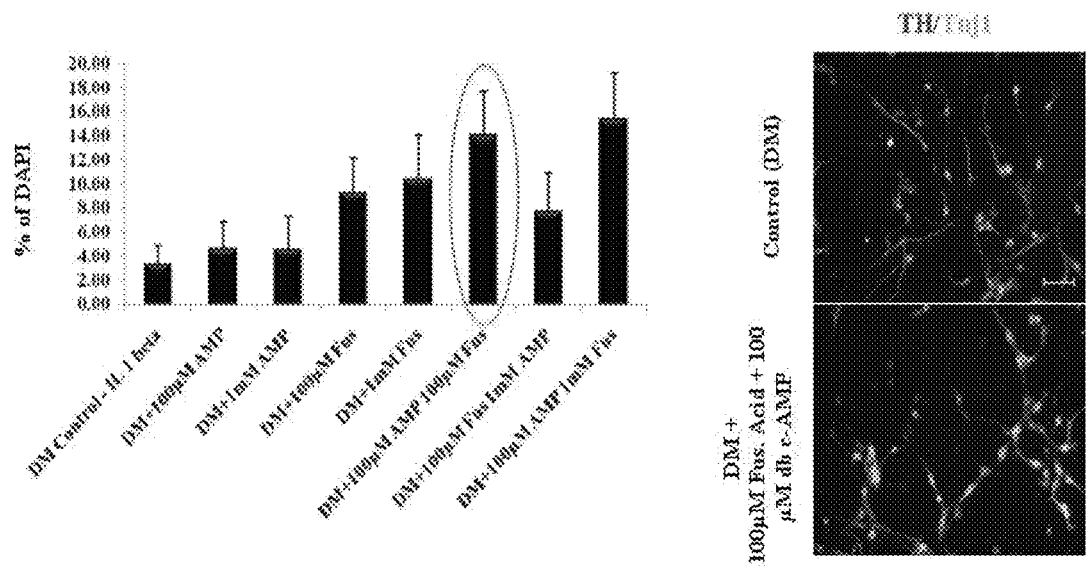
FIG. 1 shows the results obtained by counting TH and Tuj1 through the DAPI staining, after induction of the differentiation into dopaminergic neurons using various media.

The present invention provides a method for differentiating human neural progenitor cells into dopaminergic neurons, which comprises culturing human neural progenitor cells in a medium comprising fusaric acid.

The human neural progenitor cells may be obtained according to previously reported methods, for example the method described in Storch et al. 2001; and Milosevic et al. 2006, 2007. As used herein, the term "human neural progenitor cells" refers to the ex vivo cells separated from the human body, i.e., the human neural progenitor cells which are being proliferated according to conventional cell culture methods after separation from the human body. The human neural progenitor cells have stemness, and may be differentiated into neurons, astrocytes, oligodendrocytes, etc.

The differentiation method of the present invention is performed using a medium comprising fusaric acid as a differentiation-inducing agent.

The fusaric acid, whose chemical name is 5-butylpicolinic acid, has the following chemical structure of Formula 1. Fusaric acid, which is a known compound, may be prepared according to known methods or is commercially available (for example, Sigma-Aldrich etc.).

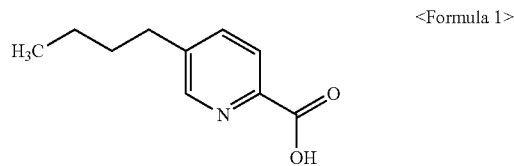

<Formula 1>

In the differentiation method of the present invention, the medium may be prepared by adding fusaric acid to a prior art medium for dopaminergic differentiation. For example, the medium may be prepared by adding fusaric acid to a prior art medium for dopaminergic differentiation comprising dibutyryl cyclic adenosine monophosphate (db-cAMP), forskolin, B27, SHH (sonic hedgehog) and FGF8 (fibroblast growth factor 8). At this time, fusaric acid may be added in a concentration of 50 µM to 4 mM. The db-cAMP, forskolin, B27, SHH, and FGF8, which are conventionally used in the art, are commercially available. For example, db-cAMP and forskolin can be purchased from Sigma; B27 can be purchased from GIBCO (trade name: B-27 minus-AO supplement); SHH and FGF8 can be purchased from R&D system and PeproTech, respectively. In an embodiment, the medium prepared by adding fusaric acid to a prior art medium for dopaminergic differentiation may be a NB medium (Neurobasal medium) comprising 50 µM to 4 mM of db-cAMP, 5 µM to 20 µM of forskolin, 0.5% to 5% of B27, 25 ng/ml to 500 ng/ml of SHH, 10 ng/ml to 200 ng/ml of FGF8, and 50 µM to 4 mM of fusaric acid. The basal medium, i.e., the NB medium may be purchased, for example from Invitrogen.

Preferably, the medium used in the differentiation method of the present invention may be a medium replacing the expensive SHH and FGF8 that are of limited use. Surprisingly, it is found by the present invention that the medium containing only fusaric acid without SHH and FGF8 exhibits higher differentiation potential into dopaminergic neurons than the medium containing all the components, i.e., SHH, FGF8, and fusaric acid.

Therefore, in the differentiation method of the present invention, the medium may be a NB medium comprising fusaric acid, db-cAMP, forskolin, and B27, preferably a NB medium comprising 50 µM to 4 mM of fusaric acid, 50 µM to 4 mM of db-cAMP, 5 µM to 20 µM of forskolin, and 0.5% w/w to 5% w/w of B27. More preferably, the medium may be a NB medium comprising 50 µM to 1 mM of fusaric acid, 50 µM to 1 mM of db-cAMP, 5 µM to 15 µM of forskolin, and 0.5% w/w to 3% w/w of B27. In an embodiment, the medium may be a NB medium comprising about 100 µM of fusaric acid, about 100 µM of db-cAMP, about 10 µM of forskolin, and about 2% w/w of B27. And also, the medium may further comprise an antibiotic such as gentamicin or an amino acid such as L-glutamine, according to necessity. Of course, the antibiotic and amino acid may be substituted by other suitable materials.

In the differentiation method of the present invention, the culturing may be performed under culture conditions used in the prior art methods. For example, the culturing may be performed at 37° C. for 7 to 14 days, preferably about 7 days. It is found by the present invention that significantly higher differentiation potential may be accomplished by culturing under a low oxygen partial pressure condition (i.e., the hypoxia condition). Therefore, in the differentiation method of the present invention, the culturing may be preferably performed under a hypoxia condition having 2% to 10% of oxygen partial pressure.

The dopaminergic neurons obtained by the differentiation method of the present invention may be harvested according to conventional methods. For example, the differentiated cells may be harvested by separating the cells with an enzyme such as Accutase (PAA), and then centrifuging the obtained cells at 1000 rpm for about 5 minutes to remove the supernatant.

The present invention also provides a medium for differentiating human neural progenitor cells into dopaminergic neurons, the medium of which is a NB media comprising fusaric acid, db-cAMP, forskolin, and B27.

The differentiation medium may be prepared by adding fusaric acid to a prior art medium for dopaminergic differentiation, as described above.

As described above, the differentiating medium may be preferably a NB medium comprising 50 µM to 4 mM of fusaric acid, 50 µM to 4 mM of db-cAMP, 5 µM to 20 µM of forskolin, and 0.5% w/w to 5% w/w of B27, more preferably a NB medium comprising 50 µM to 1 mM of fusaric acid, 50 µM to 1 mM of db-cAMP, 5 µM to 15 µM of forskolin, and 0.5% w/w to 3% w/w of B27. Most preferably, the medium may be a NB medium comprising about 100 µM of fusaric acid, about 100 µM of db-cAMP, about 10 µM of forskolin, and about 2% w/w of B27. In addition, the medium may further comprise an antibiotic such as gentamicin or an amino acid such as L-glutamine, according to necessity. Of course, the antibiotic and amino acid may be substituted by other suitable materials.

The present invention will be described in further detail with reference to the following experimental examples. These experimental examples are for illustrative purposes only and are not intended to limit the scope of the present invention.

EXAMPLE

1. Materials and Methods (1) Isolation of Human Neural Progenitor Cells (hNPCs)

Human neural progenitor cells were isolated from the human fetuses (about 14 weeks old) spontaneously aborted by mothers' uterine atonies. The fetus samples were obtained under the prior parents' informed consents. The sample collection and its use for research were approved by the ethics committee of CHA Hospital.

The human neural progenitor cells were isolated according to the method disclosed for example in Storch et al. 2001; and Milosevic et al. 2006, 2007. Ventral midbrain tissue was isolated from the brain tissue of 14 week-old fetus; and then dissociated into a single cell suspension by treating in a solution containing 0.1 mg/ml of papain and 100 µg/ml DNase at 37° C. for about 30 minutes. The suspension was washed with phosphate buffered saline (PBS) and then incubated in 50 µg/ml of antipain at 37° C. for about 30 minutes. The resulting human neural progenitor cells (hNPCs) were plated, in a monolayer (at a density of 30,000 cells/cm$^2$), onto a culture dish pre-coated with 15 µg/ml of poly-L-ornithine and 4 µg/ml of fibronectin and then cultivated.

(2) Differentiation and Isolation

For dopaminergic differentiation, hNPCs were plated onto a culture dish pre-coated with 15 µg/ml of poly-L-ornithine and 4 µg/ml of fibronectin at a density of 30,000 cells/cm$^2$; and after 2 or 3 days the cells were cultured in a NB medium comprising differentiation-inducing agents such as 2% of B27 minus-AO supplement (GIBCO), 10 µM of forskolin, 1 mM of db-cAMP and 1 mM of fusaric acid, at 37° C. for 7 days, unless otherwise described.

The differentiated cells, i.e., dopaminergic neurons, were harvested according to the followings: The culture medium was removed from the culture dish. Cells were washed with a buffer solution and then treated with Accutase (PAA) for 30 minutes to detach cells. The cells were washed again with a buffer solution and then centrifuged at 1000 rpm for about 5 minutes. The supernatant was removed to harvest differentiated dopaminergic neurons.

(3) RNA Extraction, Reverse Transcription and Quantitative Real-Time PCR

Total cellular RNAs were extracted from the hNPC, using Trizol and chloroform. cDNAs were synthesized from 500 ng of the total RNAs, using RNA Superscript II RTase, Oligo-d (T) primers, DTT and dNTPs, according to the manufacturer's protocol. The PCR was performed in a final volume of 20 µl containing 1 µl of cDNA and 1 µl of 10 pM primers, using a SYBR-Green mixture. The expressions of TH, DAT, GFAP, Nurr1, Tuj1, and Lmx1a were analyzed, using RPL22 as an internal control. The quantitative real-time PCR was performed using the LightCycler System. The amplification was monitored and analyzed through measuring the binding of the fluorescent dye SYBR Green to double-stranded DNA. The target DNAs were amplified by performing total 40 cycles, under the conditions at 95° C. for 10 seconds, at 60° C. for 10 seconds, at 72° C. for 20 seconds. Final extension was performed at 72° C. for 10 minutes. Results were expressed relative to the gene RPL-22 by comparative Ct method. The primers used in the PCR are described in Table 1.

TABLE 1

| Gene | Primer | Sequence | SEQ. ID. | product size |
|---|---|---|---|---|
| TH | Sense primer | 5'-agccctaccaagaccagacg-3' | 1 | 132 bp |
|  | Antisense primer | 5'-gcgtgtacgggtcgaactt-3' | 2 |  |
| Tuj1 | Sense primer | 5'-gggcctttggacatctcttc-3' | 3 | 90 bp |
|  | Antisense primer | 5'-cctccgtgtagtgacccttg-3' | 4 |  |
| Nestin | Sense primer | 5'-cagctggcgcacctcaagatg-3' | 5 | 208 bp |
|  | Antisense primer | 5'-agggaagttgggctcaggactgg-3' | 6 |  |
| Sox2 | Sense primer | 5'-gccgagtggaaactttgtc-3' | 7 | 264 bp |
|  | Antisense primer | 5'-gttcatgtgcgcgtaactgt-3' | 8 |  |
| Musashi1 | Sense primer | 5'-acagcccaagatggtgactc-3' | 9 | 191 bp |
|  | Antisense primer | 5'-ccacgatgtcctcactctca-3' | 10 |  |
| Lmx1a | Sense primer | 5'-tgcttagcccaggactttca-3' | 11 | 136 bp |
|  | Antisense primer | 5'-tgaagatggagggagagctg-3' | 12 |  |
| PAX6 | Sense primer | 5'-ccaaagtggtggacaagattgcc-3' | 13 | 419 bp |
|  | Antisense primer | 5'-taactccgcccattcactgacg-3' | 14 |  |
| VMAT2 | Sense primer | 5'-atccagaccaccagaccagag-3' | 15 | 616 bp |
|  | Antisense primer | 5'-ccccatccaagagcaccaagg-3' | 16 |  |
| Pitx3 | Sense primer | 5'-tgtcattctcagatgcaggcac-3' | 17 | 400 bp |
|  | Antisense primer | 5'-tgaccgagttaaggcgaac-3' | 18 |  |
| DAT | Sense primer | 5'-tgcgtgccacatcaataaca-3' | 19 | 170 bp |
|  | Antisense primer | 5'-aacatccttcactcagtattgctaa-3' | 20 |  |
| Nurr1 | Sense primer | 5'-cgaccaagacctgcttttg-3' | 21 | 125 bp |
|  | Antisense primer | 5'-attgcaacctgtgcaagacc-3' | 22 |  |
| GIRK2 | Sense primer | 5'-gggcaaaccctctcttctc-3' | 23 | 212 bp |
|  | Antisense primer | 5'-ggcactttgcactttcatca-3' | 24 |  |
| Lmx1a | Sense primer | 5'-tgcttagcccaggactttca-3' | 25 | 136 bp |
|  | Antisense primer | 5'-tgaagatggagggagagctg-3' | 26 |  |
| RPL22 | Sense primer | 5'-cacgaaggaggagtgactgg-3' | 27 | 116 bp |
|  | Antisense primer | 5'-tgtggcacaccactgacatt-3' | 28 |  |

(4) Immunocytochemistry hNPCs were washed with PBS three times and then fixed with 4% paraformaldehyde in PBS for 10 minutes. The cells were washed with PBS three times and then blocked by reacting with 3% Normal goat serum, 0.2% Triton X-100 and 1% BSA in PBS at room temperature for 1 hour. After incubation with primary antibodies, i.e., anti-TH (rabbit anti-TH, Pelfreez), anti-Tuj1 (mouse anti-Tuj1 Millipore, Calif. USA), anti-nestin (rabbit anti-nestin, COVANCE, CA, USA), anti-GFAP (mouse anti-GFAP Millipore, Calif. USA), anti-Ki67 (mouse anti-Ki67, Leica), anti-04 (mouse anti-04, Millipore), anti-Sox2 (rabbit anti-Sox2, Abcam), anti-VMAT2 (rabbit anti-VMAT2, Abcam), anti-Pitx3 (rabbit anti-Pitx3, Millipore), anti-DAT (rabbit anti-DAT, Santa Cruz), anti-Nurr1 (rabbit anti-Nurr1, Santa Cruz), anti-NeuN (mouse anti-NeuN, Millipore), anti-GIRK2 (rabbit anti-GIRK2, Alomone lab), anti-Cal28K (mouse anti-Cal28K, Sigma), anti-Glutamate (rabbit anti-Glutamate, Sigma), anti-GABA (rabbit anti-GABA, Sigma), anti-ChAT (mouse anti-ChAT, Millipore) and anti-5-HT (rabbit anti-5-HT, ImmunoStar) at 4° C. overnight, the cells washed with PBS three times and then incubated with secondary antibodies, i.e., anti-mouse (Alexa Fluor™ 488), anti-mouse (Alexa Fluor™ 594), anti-rabbit (Alexa Fluor™ 488), and anti-rabbit (Alexa Fluor™ 594) at room temperature for 60 hours, followed by counterstaining with DAPI (4',6-Diamidino-2-phenylindole).

(5) Immunoblotting

Proteins were extracted with a RIPA buffer solution [10 mM HEPES-KOH (pH 7.9), 10 mM KCl, 1.5 mM $MgCl_2$, 0.1% NP-40] supplemented with protease inhibitors (PI) (Roche Molecular Biochemicals). Protein concentration was determined using a BCA method (Pierce). The proteins were resolved in a SDS-10% polyacrylamide gel and then transferred to a PVDF membrane. The membranes were blocked with 5% skim milk in a TBS-T buffer solution at room temperature for 2 hours, and then incubated with primary antibodies, i.e., anti-TH (rabbit anti-TH, Pelfreez, 1:1000), anti-Tuj1 (rabbit anti-Tuj1 COVANCE, 1:5000), anti-Nestin (rabbit anti-Nestin, Abcam, 1:1000), anti-Sox2 (rabbit anti-Sox2, Abcam, 1:1000), anti-Bcl2 (mouse anti-Bcl2, Santa Cruz, 1:200), anti-PCNA (mouse anti-PCNA, Santa Cruz, 1:1000), anti-VMAT2 (rabbit anti-VMAT2, Abcam, 1:1000), anti-Pitx3 (rabbit anti-Pitx3, Millipore, 1:2000), anti-DAT (rabbit anti-DAT, Santa Cruz, 1:200), anti-Nurr1 (rabbit anti-Nurr1, Santa Cruz, 1:250), anti-Actin (rabbit anti-Actin, Santa Cruz, 1:5000) at 4° C. overnight. The membrane was incubated with anti-mouse and anti-rabbit secondary antibodies conjugated with HRP (horse radish peroxidase) at room temperature for 1 hour, and then exposed with chemiluminescence western blot detection reagents.

Figure 2:
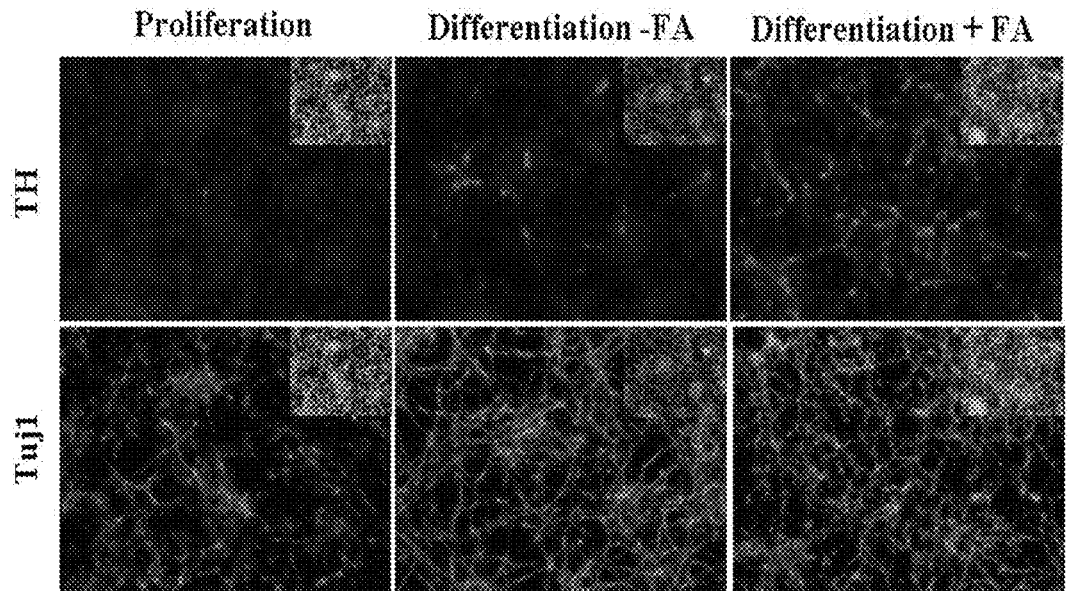
FIG. 2 shows the results obtained by measuring the expression levels of TH and Tuj1, after proliferation of hNPCs, followed by induction of the differentiation into neurons in media with or without 100 µM fusaric acid.
Figure 3:
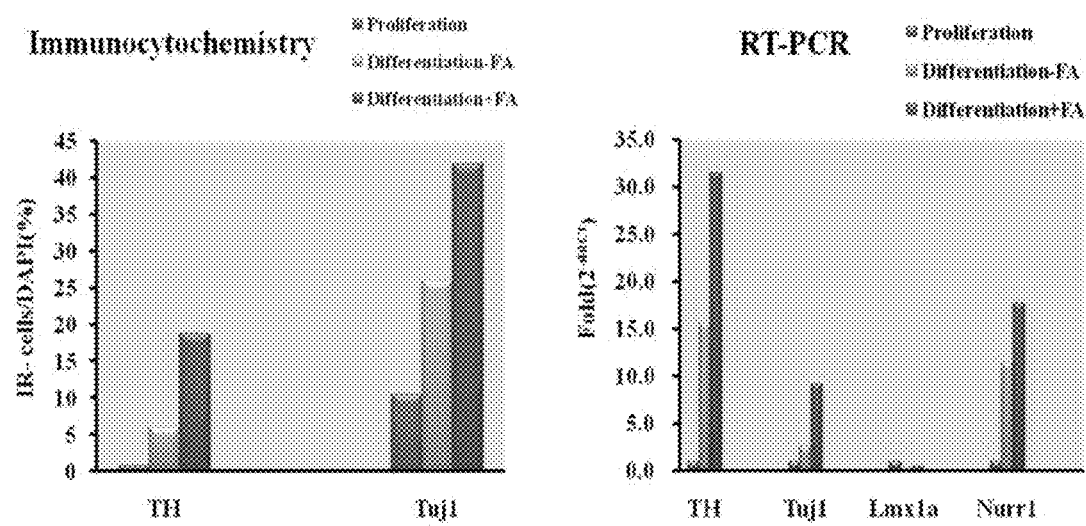
FIG. 3 shows the results obtained by performing immunocytochemistry and RT-PCR analyses, after proliferation of hNPCs, followed by induction of the differentiation into neurons in media with or without 100 µM fusaric acid.

2. Results and Discussion (1) Evaluation of Differentiation Conditions (Medium Conditions)

hNPCs were differentiated into dopaminergic neurons in media obtained by adding interleukin 1 beta, db-cAMP, and fusaric acid (Fus), in various concentrations and combinations, to a Neurobasal medium [differentiation medium (DM) control]. TH (a dopaminergic neuron marker) and Tuj1 (a neural marker) were measured through the DAPI staining (FIG. 1). From the results of FIG. 1, it can be seen that the use of the culture medium containing db-cAMP and fusaric acid showed the highest expression levels of TH and Tuj1, i.e., the highest differentiation potential. And also, it can be seen that, when db-cAMP and fusaric acid were used in a concentration of 100 μM respectively, the highest differentiation potential was obtained.

hNPCs were proliferated in a DMEM/F12 (1:1) Glutamax medium, and then differentiated to neurons in a Neurobasal (NB) medium containing 2% of B-27 minus-AO supplement (GIBCO), 10 μM of forskolin, and 1 mM of db-cAMP, along with or without 100 μM of fusaric acid. After induction of the differentiation, the expression levels of TH and Tuj1 were measured (FIG. 2). The results of the immunocytochemistry and RT-PCR analyses were shown in FIG. 3. From the results of FIGS. 2 and 3, it can be seen that, when fusaric acid was added, TH (a dopaminergic neuron marker) was remarkably high expressed. And also, when fusaric acid was added, the expression of Tuj1 (a neuronal marker) was also increased.

Figure 4:
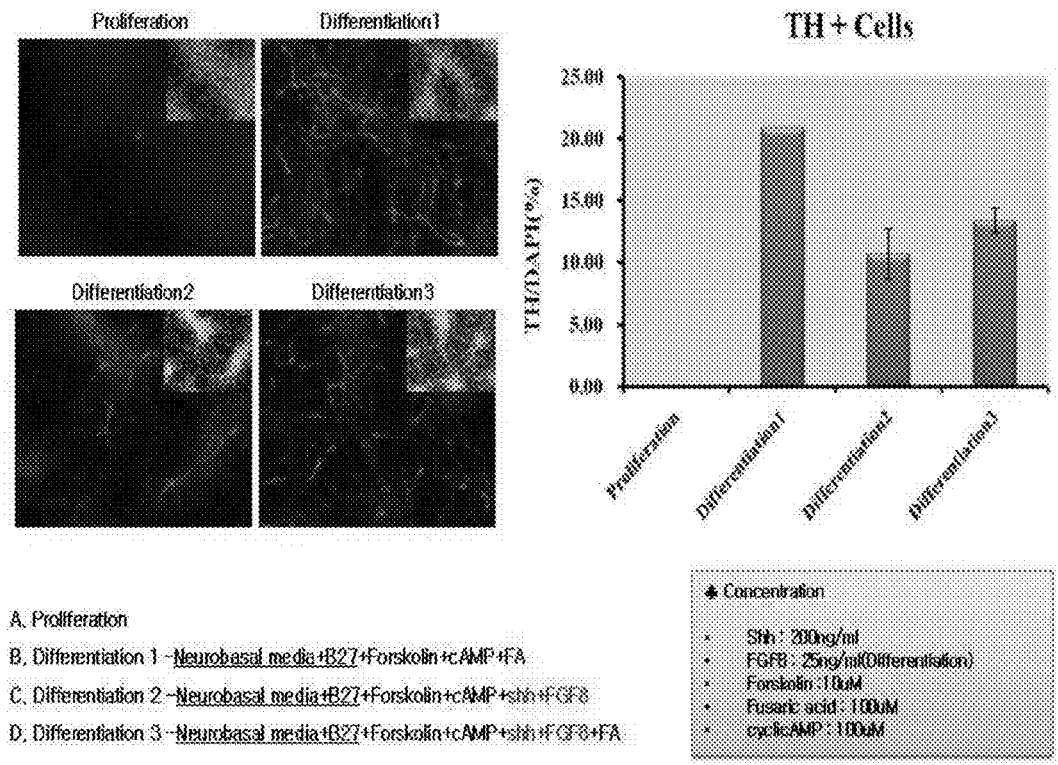
FIG. 4 shows the results obtained by measuring the expression levels of TH in the cells, after induction of the differentiation into dopaminergic neurons using media with different differentiation-inducing agents.

In order to evaluate substitution potential for the expensive SHH and FGF8 that are of limited use as a differentiation-inducing agent, hNPCs were proliferated in a DMEM/F12 (1:1) Glutamax medium. After induction of the differentiation in a Neurobasal (NB) medium (Invitrogen) using 2% of B-27, 200 ng/ml of SHH, 25 ng/ml of FGF8, 10 μM of forskolin, 100 μM of fusaric acid, and 100 μM of db-cAMP, the expression levels of TH were measured (FIG. 4). From the results of FIG. 4, it can be seen that, when fusaric acid was treated instead of SHH and FGF8, the cells were differentiated most effectively into dopaminergic neurons. And also, the differentiation into dopaminergic neurons was more increased, even when fusaric acid was added in addition to SHH and FGF8.

Therefore, from the results of FIGS. 1 to 4, it can be seen that induction of the differentiation of hNPCs in a medium containing fusaric acid can accomplish significantly high differentiation potential into dopaminergic neurons.

Figure 5:
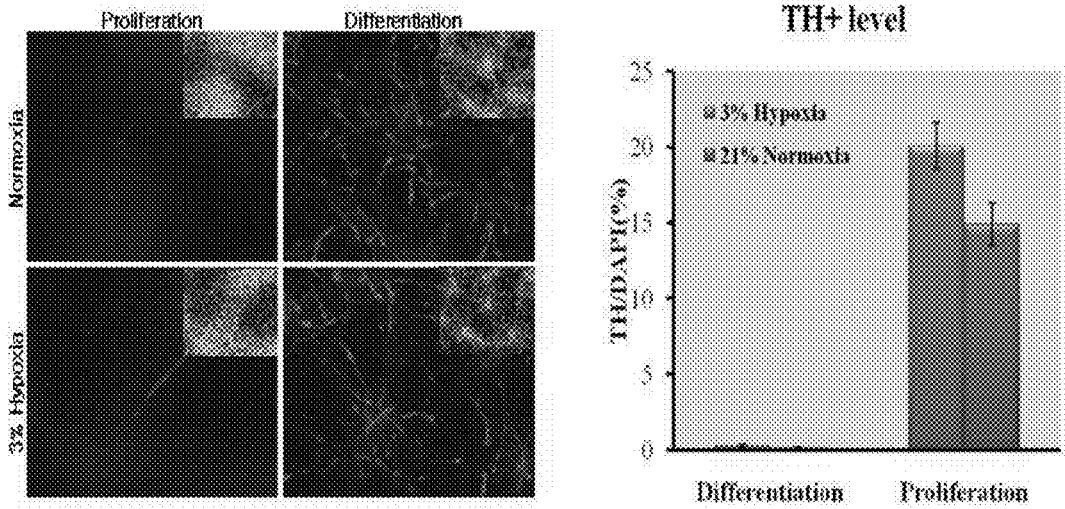
FIG. 5 shows the results obtained by measuring the differentiation potentials in hypoxia and in normoxia, respectively.

(2) Evaluation of Differentiation Conditions (Culture Conditions)

hNPCs were proliferated in a DMEM/F12 (1:1) Glutamax medium, and then differentiated in a Neurobasal (NB) medium (Invitrogen) containing 2% of B-27, 10 μM of forskolin, 100 μM of fusaric acid, and 100 μM of db-cAMP, under the hypoxia condition (3% of oxygen partial pressure) or the normoxia condition (21% of oxygen partial pressure). After induction of the differentiation, the expression levels of TH were measured (FIG. 5). From the results of FIG. 5, it can be seen that the cells were differentiated more efficiently into dopaminergic neurons in hypoxia than in normoxia.

(3) Analysis on Neuroprotective Effects of Fusaric Acid

It is known that 1-methyl-4-phenylpyridium (MPP) induces cytotoxicity on dopaminergic neurons. Therefore, we evaluated functions of fusaric acid during the differentiation, through inducing differentiation in the presence of MPP (FIG. 6).

Figure 6:
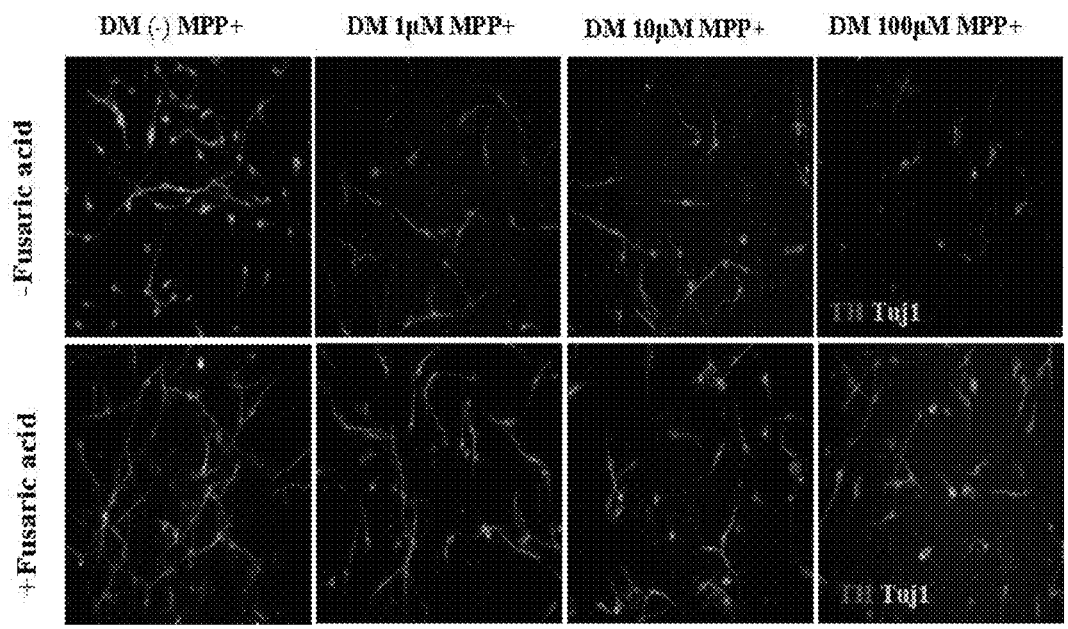
FIG. 6 shows the results obtained by measuring the effects of fusaric acid, when differentiation was induced in the presence of MPP.

From the results of FIG. 6, it can be seen that more TH-expressing cells survived when the differentiation was induced in the medium containing fusaric acid, even under the MPP treatment. In addition, the neuronal marker, i.e., Tuj1, was also relatively more expressed. These results suggest that fusaric acid has neuroprotective activity, thereby affecting viability of the TH-expressing cells, which makes relatively more dopaminergic neurons survive.

(4) Evaluation of Differentiation/Proliferation hNPCs were proliferated in a DMEM/F12 (1:1) Glutamax medium, and then continuously cultivated under the condition of 3% oxygen partial pressure, while changing the medium every other day. The hNPCs obtained at early passage (passage 7), middle passage (passage 11), and later passage (passage 17) were differentiated in NB medium (Invitrogen) containing 2% of B-27, 10 μM of forskolin, 100 μM of fusaric acid, and 100 μM of db-cAMP, under the condition of 3% oxygen partial pressure, for 7 days.

Figure 7:
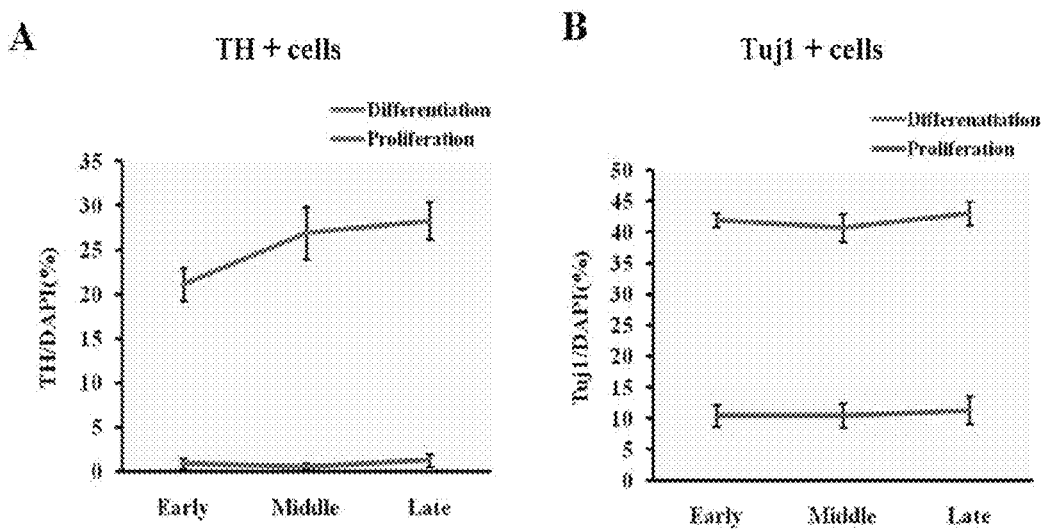
FIG. 7 shows the results obtained by measuring the expression levels of TH and Tuj1, after proliferation and subculture of hNPCs, followed by induction of the differentiation of the hNPCs at early passage (passage 7), middle passage (passage 11), and later passage (passage 17).
Figure 8:
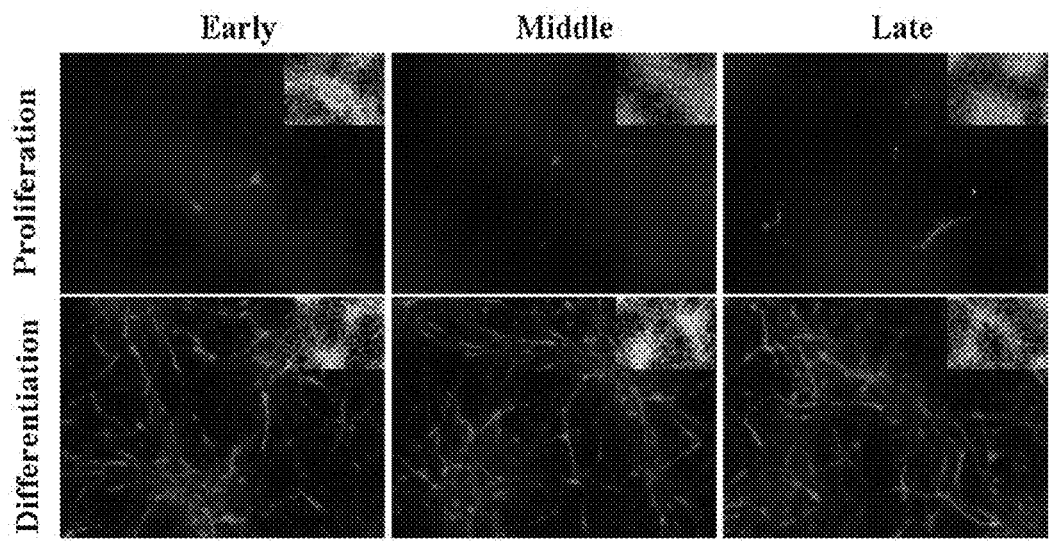
FIG. 8 shows the results obtained by measuring the expression levels of TH in the respective cells through immunocytochemistry, after proliferation and subculture of hNPCs, followed by induction of the differentiation of the hNPCs at early passage (passage 7), middle passage (passage 11), and later passage (passage 17).
Figure 9:
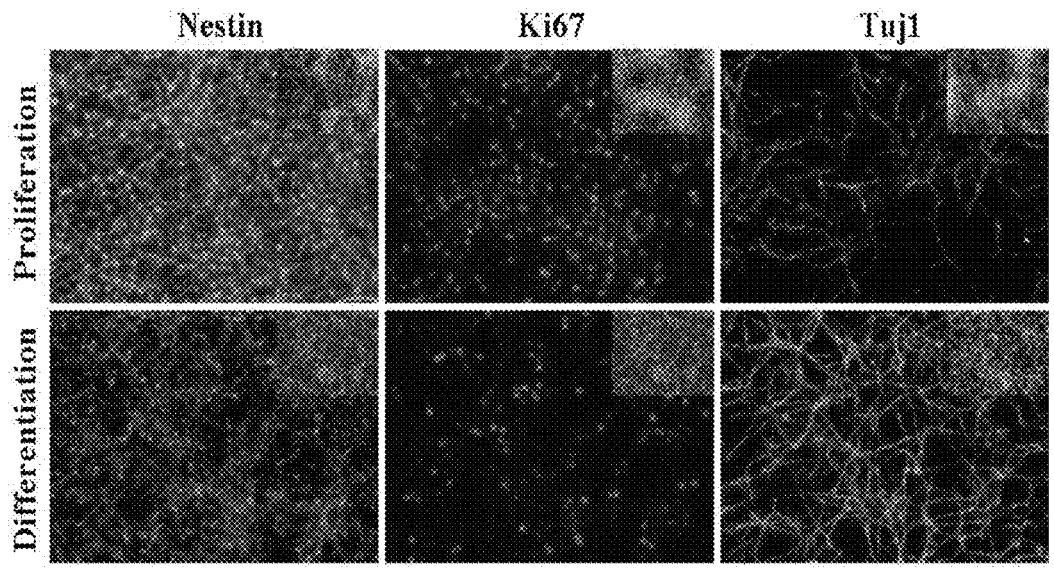
FIG. 9 shows the results obtained by measuring the expression levels of nestin (a neural stem cell marker), Ki67 (a proliferative cell marker), Tuj1 (a neuronal marker) in the respective cells through immunocytochemistry, after proliferation and subculture of hNPCs, followed by induction of the differentiation of the respective hNPCs at early passage (passage 7), middle passage (passage 11), and later passage (passage 17).

Expression levels of TH and Tuj1 were measured from the respective cells (i.e., the proliferated cells and the differentiated cells) obtained at early passage (passage 7), middle passage (passage 11), and later passage (passage 17) (FIG. 7). The expression levels of TH in the cells were measured via immunocytochemistry (FIG. 8). In addition, expression levels of nestin (a neural stem cell marker), Ki67 (a proliferative cell marker), Tuj1 (a neuronal marker) were measured using immunocytochemistry (FIG. 9). The TH-positive cells in the cells differentiated according to the present invention were increased more than 20%, in comparison with the non-differentiated cells (i.e., the proliferated cells). The differentiation potential was increased up to about 30%, with the increase of the passage (see FIG. 7 A). The Tuj1-positive cells after the differentiation were also increased up to 40~45% from about 10% (before the differentiation), which was not changed in the later passages (see FIG. 7 B). The results were the same as in the immunocytochemistry on the TH-positive cells; and the differentiation potential was increased, with the increase of the passage (see FIG. 8). After the differentiation, the expressions of nestin and ki67 were reduced, while the expression of Tuj1 was increased (see FIG. 9). These results suggest that, as differentiation is proceeding, the proliferating cells not only gradually lose their stemness but also are differentiated into mature neurons.

Figure 10:
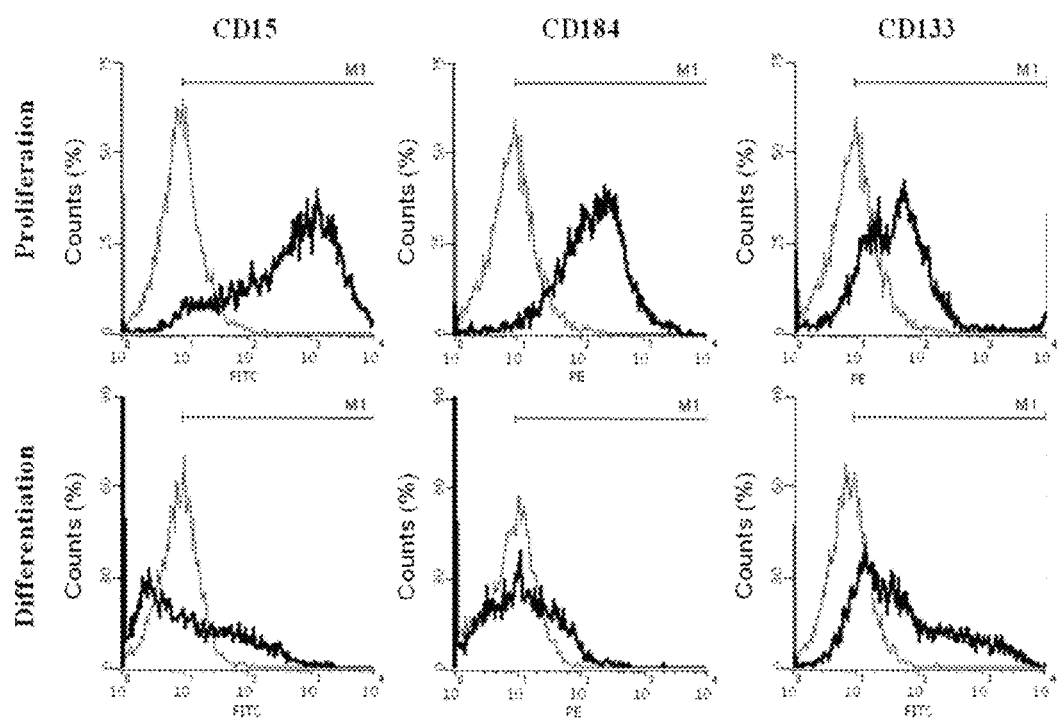
FIG. 10 shows the results obtained by performing FACS analyses on the hNPCs at the early passage (passage 7) before and after the differentiation for 7 days.
Figure 11:
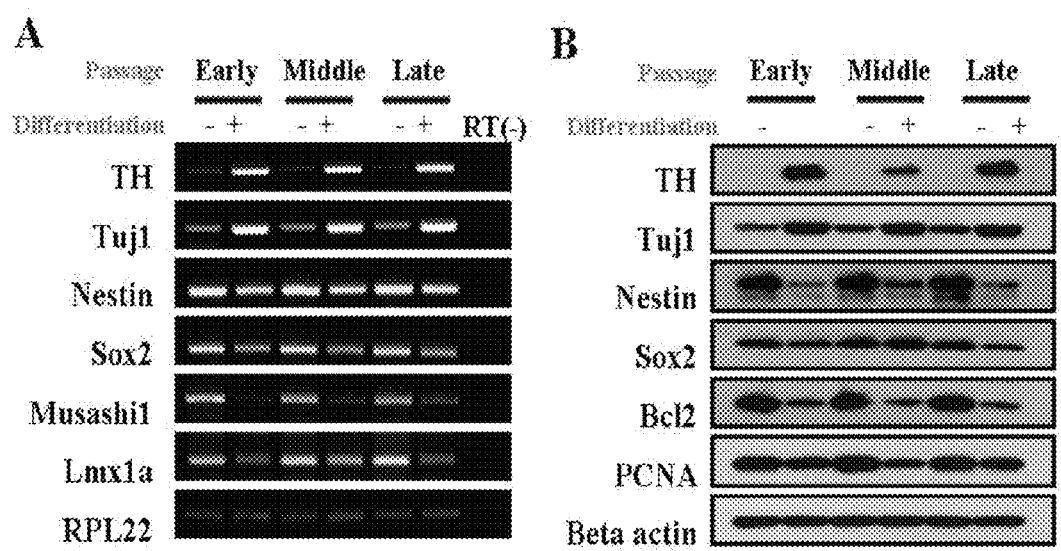
FIG. 11 shows the results obtained by performing RT-PCR and Western blot analyses on the resulting cells, after proliferation and subculture of hNPCs, followed by induction of the differentiation of the respective hNPCs at early passage (passage 7), middle passage (passage 11), and later passage (passage 17).

And also, as a result of the FACS analysis performed on the hNPCs at early passage (passage 7), the surface markers of neural stem cells (i.e., CD15, 184, and 133) were significantly reduced after the differentiation, in comparison with before the differentiation (see FIG. 10). These results show that the cells are losing their stemness and being changed to differentiated cells. And also, as the results of the RT-PCR analyses, when the passage becomes increased, the expression of TH (a dopaminergic neuron marker) was normally maintained; the expression of Tuj1 (a neural cell marker) was increased; and the expressions of nestin, sox2, and musashil (neural stem cell markers) were decreased (see FIG. 11 A). At the Western blot analyses, when the passage becomes increased, the expression of TH was normally maintained; the expression of Tuj1 was increased; and the expressions of nestin and sox2 were decreased (see FIG. 11B), the results of which are the same as in the RT-PCR analyses. And also, Bcl2 (an anti apototic marker) and PCNA (a proliferation marker) were also reduced (see FIG. 11 B).

Therefore, from the results of FIGS. 7 to 11, it can be seen that, when cells were cultured to the later passage and then differentiated in the said differentiation medium, the differentiation thereof was induced in the same differentiation potential as in the cells at the early passage.

(5) Characterization of Differentiated Dopaminergic Neurons hNPCs were differentiated in a NB medium (Invitrogen) containing 2% of B-27, 10 µM of forskolin, 100 µM of fusaric acid, and 100 µM of db-cAMP under the condition of 3% oxygen partial pressure for 14 days.

Figure 12:
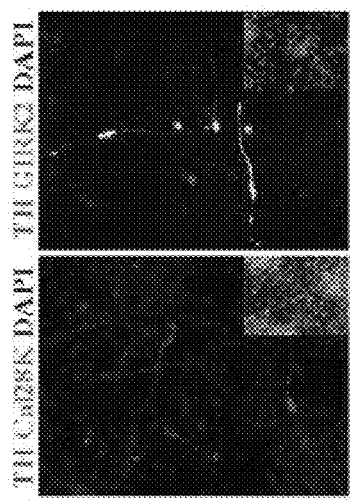
FIG. 12 shows the results obtained by characterizing the cells differentiated according to the differentiation method of the present invention, through immunocytochemistry.
Figure 12:
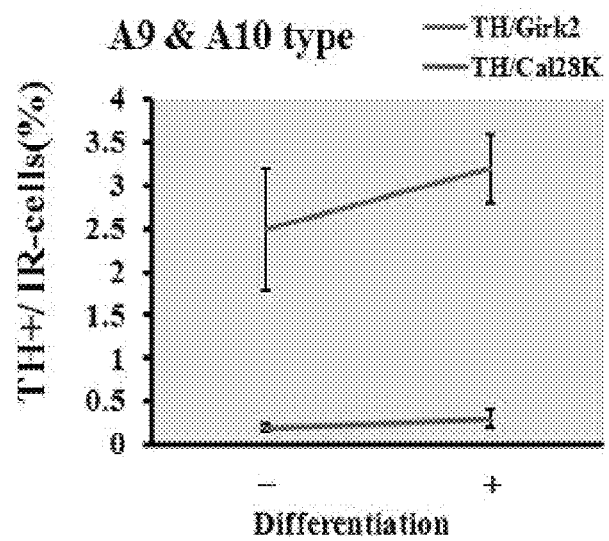

From the resulting cells, the expressions of TH and mature dopaminergic neuron markers (NeuN, VMAT2, Nurr1, and Pitx3) were measured through immunocytochemistry (FIG. 12 A). In order to identify type of the TH-expressing cells (i.e., type A9 or type A10), the expressions of Girk2 and cal28K were measured through immunocytochemistry (FIG. 12 B). If both Girk2 and TH are co-expressed, the cells are regarded as type A9. If both cal28K and TH are co-expressed, the cells are regarded as type A10. From the results of FIG. 12, it can be seen that the dopaminergic neurons obtained according to the differentiation method of the present invention are mature dopaminergic neurons of A9 type.

Figure 13:
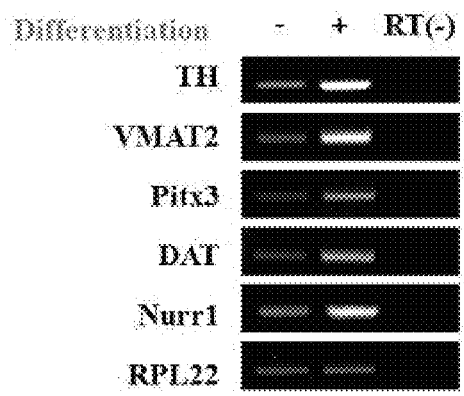
FIG. 13 shows the results obtained by characterizing the cells differentiated according to the differentiation method of the present invention, through RT-PCR, Western blot analyses, and immunocytochemistry.
Figure 13:
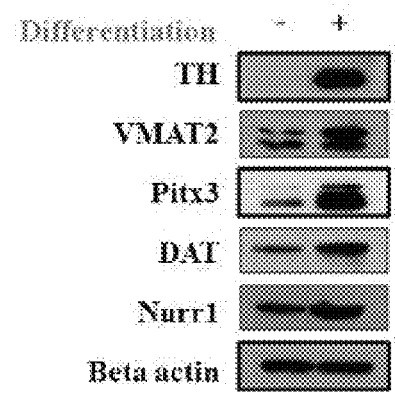
Figure 13:
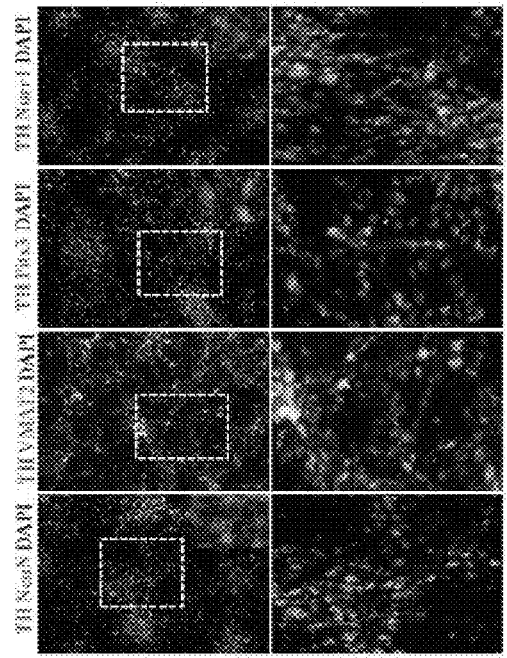

And also, as the results of the RT-PCR analyses, the mature dopaminergic neuron markers such as VMAT2, Pitx3, DAT, Nurr1, as well as TH, were remarkably increased after the differentiation (+), in comparison with before the differentiation (−) (see FIG. 13 A). At the Western blot analyses, the mature dopaminergic neuron markers such as VMAT2, Pitx3, DAT, Nurr1, as well as TH, were remarkably increased after the differentiation (+), in comparison with before the differentiation (−) (see FIG. 13 B). These results are the same as the results of immunocytochemistry (see FIG. 13 C). Through immunocytochemistry, it was confirmed that the mature dopaminergic neuron markers were remarkably increased from the 7th day to the 14th day after induction of the differentiation.

Figure 14:
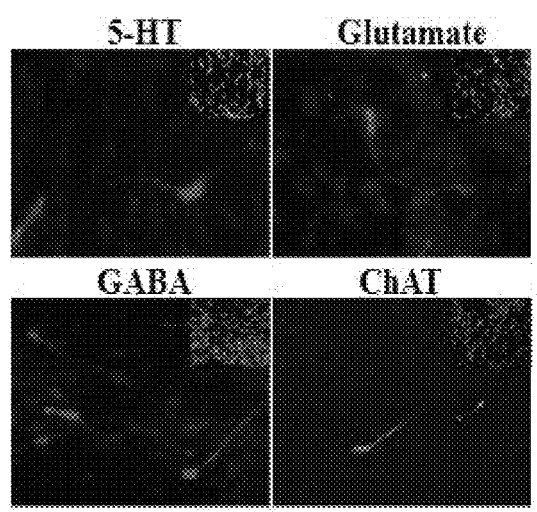
FIG. 14 shows the results obtained by measuring the expressions of other subtypes of neurons, i.e., glutamate, GABA, ChAT and serotonine through immunocytochemistry, when differentiation was induced according to the differentiation method of the present invention.
Figure 14:
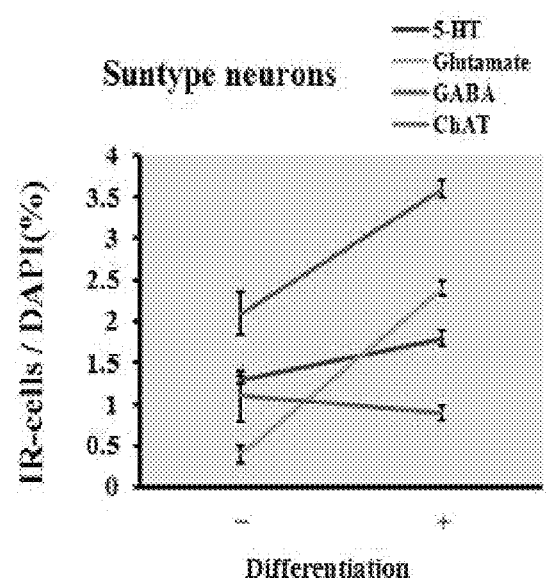

And also, in order to indentify differentiation to other subtypes of neurons, the expressions of glutamate, GABA, ChAT and serotonine were measured through immunocytochemistry (FIG. 14). From the results of FIG. 14, it can be seen that other subtypes of neurons were expressed in significantly lower amounts than the dopaminergic neurons.

REFERENCE

1: Bjorklund, A. et al. Reconstruction of the nigro-striatal dopamine pathway by intra-cerebral nigral transplants, Brain Res. 1979; 177:555-560
2: Perlow, M., et al. Brain grafts reduce motor abnormalities produced by destruction of nigrostriatal dopamine system. Science 1979; 204:643-647
3: Brain J. Snyder. et al. Stem cell treatment for parkinson's disease: an update for 2005. Current Opinion in Neurology. 2005; 18:376-385
4: Storch A. et al Midbrain-derives neural stem cells: from basic science to therapeutic approaches. Cell tissue Res. 2004; 318:15-22
5: Yang M. et al. Neural stem cells spontaneously express dopaminergic traits after transplantation into the intact or 6-hydrodopamine lesioned rat. Exp Neural, 2002; 177:50-60
6: Sanchez-Pernaute, R. et al. In vitro generation and transplantation of precursor-derived human dopamine neurons. J. Neurosic. Res. 2001; 65(4). 284-288
7: Riaz, S. S. et al. The differentiation potential of human foetal neuronal progenitor cells in vitro. Brain Res. Dev. Brain Res. 2004; 153(1), 39-51
8: Jaroslaw Maciaczyk et al. Combined use of BDNF, ascorbic acid, low oxygen, and prolonged differentiation time generates tyrosine hydroxylase-expressing neurons after long-term in vitro expansion of human fetal midbrain precursor cells. Experimental Neurology. 2008; 213:354-362

The invention claimed is:

1. A method for differentiating human neural progenitor cells into dopaminergic neurons, which comprises culturing human neural progenitor cells in a medium comprising fusaric acid.

2. The method according to claim 1, wherein the medium is prepared by adding fusaric acid to a medium for dopaminergic differentiation comprising dibutyryl cyclic adenosine monophosphate (db-cAMP), forskolin, B27, sonic hedgehog (SHH), and fibroblast growth factor 8 (FGF8).

3. The method according to claim 1, wherein the medium is a NB medium comprising fusaric acid, db-cAMP, forskolin, and B27.

4. The method according to claim 3, wherein the medium is a NB medium comprising 50 μM to 4 mM of fusaric acid, 50 μM to 4 mM of db-cAMP, 5 μM to 20 μM of forskolin, and 0.5% w/w to 5% w/w of B27.

5. The method according to claim 3, wherein the medium is a NB medium comprising 100 μM of fusaric acid, 100 μM of db-cAMP, 10 μM of forskolin, and 2% w/w of B27.

6. The method according to claim 1, wherein the culturing is performed under a hypoxia condition having 2% to 10% of oxygen partial pressure.

7. A medium for differentiating human neural progenitor cells into dopaminergic neurons, the medium of which is a NB media comprising fusaric acid, db-cAMP, forskolin, and B27.

8. The medium according to claim 7, wherein the medium is a NB medium comprising 50 μM to 4 mM of fusaric acid, 50 μM to 4 mM of db-cAMP, 5 μM to 20 μM of forskolin, and 0.5% w/w to 5% w/w of B27.

9. The method according to claim 8, wherein the medium is a NB medium comprising 100 μM of fusaric acid, 100 μM of db-cAMP, 10 μM of forskolin, and 2% w/w of B27.

* * * * *